(12) United States Patent
Hausmann et al.

(10) Patent No.: US 8,394,385 B2
(45) Date of Patent: Mar. 12, 2013

(54) OPTIMIZED EARLY-LATE PROMOTER COMBINED WITH REPEATED VACCINATION FAVORS CYTOTOXIC T CELL RESPONSE AGAINST RECOMBINANT ANTIGEN IN MVA VACCINES

(75) Inventors: Jürgen Hausmann, Gundelfingen (DE); Karen Baur, Munich (DE); Kay Brinkmann, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 396 days.

(21) Appl. No.: 12/719,987

(22) Filed: Mar. 9, 2010

(65) Prior Publication Data

US 2010/0233203 A1    Sep. 16, 2010

Related U.S. Application Data

(60) Provisional application No. 61/159,857, filed on Mar. 13, 2009.

(30) Foreign Application Priority Data

Jul. 28, 2009    (EP) ..................................... 09009759

(51) Int. Cl.
| | |
|---|---|
| A61K 39/275 | (2006.01) |
| A61K 39/285 | (2006.01) |
| A61K 39/12 | (2006.01) |
| A61K 48/00 | (2006.01) |
| A01N 63/00 | (2006.01) |
| A01N 65/00 | (2009.01) |
| C12Q 1/70 | (2006.01) |
| C12N 15/00 | (2006.01) |

(52) U.S. Cl. ............... 424/232.1; 424/199.1; 424/204.1; 424/205.1; 424/93.2; 435/5; 435/93.1; 435/93.2; 435/320.1

(58) Field of Classification Search ........................ None
See application file for complete search history.

(56) References Cited

U.S. PATENT DOCUMENTS 6,761,893 B2    7/2004    Chaplin et al.

FOREIGN PATENT DOCUMENTS

| CA | 2104649 A1 | 2/1994 |
|---|---|---|
| EP | 1536015 A1 | 6/2005 |
| WO | 02/42480 A2 | 5/2002 |
| WO | WO2010102822 A1 | 9/2010 |

OTHER PUBLICATIONS

Assarsson et al., Kinetic analysis of a complete poxvirus transcriptome reveals an immediate-early class of genes, Proc. Natl. Acad. Sci. 105:2140-2145 (2008).
Bronte et al., Antigen expression by dendritic cells correlates with the therapeutic effectiveness of a model recombinant poxvirus tumor vaccine, Proc. Natl. Acad. Sci. 94:3183-3188 (1997).
Broyles, Vaccinia virus transcription, Journal of General Virology 84:2293-2303 (2003).
Carroll et al., Host Range and Cytopathogenicity of the Highly Attenuated MVA Strain of Vaccinia Virus: Propagation and Generation of Recombinant Viruses in a Nonhuman Mammalian Cell Line, Virology 238:198-211 (1997).
Chakrabarti et al., Compact, Synthetic, Vaccinia Virus Early/Late Promoter for Protein Expression, BioTechniques 23:1094-1097 (Dec. 1997).
Cochran et al., In Vitro Mutagenesis of the Promoter Region for a Vaccinia Virus Gene: Evidence for Tandem Early and Late Regulatory Signals, Journal of Virology 54:30-37 (1985).
Cosma et al., Therapeutic vaccination with MVA-HIV-1 nef elicits Nef-specific T-helper cell responses in chronically HIV-1 infected individuals, Vaccine 22:21-29 (2003).
Coupar et al., Temporal regulation of influenza hemagglutinin expression in vaccinia virus recombinants and effects on the immune response, Eur. J. Immunol. 16: 1479-1487 (1986).
Davison et al., Structure of Vaccinia Virus Early Promoters, J. Mol. Biol. 210:749-769 (1989).
Davison et al., Structure of Vaccinia Virus Late Promoters, J. Mol. Biol. 210:771-784 (1989).
Di Nicola et al., Immunization of Patients with Malignant Melanoma with Autologous CD341 Cell-Derived Dendritic Cells Transduced Ex Vivo with a Recombinant Replication-Deficient Vaccinia Vector Encoding the Human Tyrosinase Gene: A Phase I Trial, Human Gene Therapy 14:1347-1360 (Sep. 20, 2003).
Di Nicola et al., Boosting T Cell-Mediated Immunity to Tyrosinase by Vaccinia Virus-Transduced, CD34+-Derived Dendritic Cell Vaccination: A Phase I Trial in Metastatic Melanoma, Clinical Cancer Research 10:5381-5390 (2004).
Funahashi et al., Increased Expression In Vivo and In Vitro of Foreign Genes Directed by A-Type Inclusion Body Hybrid Promoters in Recombinant Vaccinia Viruses, Journal of Virology 65:5584-5588 (1991).
Harrer et al., Therapeutic Vaccination of HIV-1-infected patients on HAART with a recombinant HIV-1 nef-expressing MVA:safety, immunogenicity and influence on viral load during treatment, Antivaral Therapy 10:285-300 (2005).
Hirschmann et al., Mutational Analysis of a Vaccinia Virus Intermediate Promoter In Vivo and In Vitro, Journal of Virology 64:6063-6069 (1990).
Jin et al., Construction of a vaccinia viruss A-type inclusion body protein, tandemly repeated mutant 7.5 kDA protein, and hemagglutinin gene promoters support high levels of expression, Arch Virol 138:315-330 (1994).
Kastenmuller et al., Cross-competition of CD8 + T cells shapes the immunodominance hierarchy during boost vaccination, J. Exp. Med. 204:2187-2198 (2007).

(Continued)

*Primary Examiner* — Louise Humphrey
(74) *Attorney, Agent, or Firm* — Law Office of Salvatore Arrigo and Scott Lee, LLP

(57) ABSTRACT

The invention is drawn to compositions and methods for the induction of a strong CD8 T cell response to a specific antigen(s). The combination of an early/late hybrid promoter directing strongly enhanced early expression of a neoantigen with at least three immunization rounds resulted in a highly efficient neoantigen-specific CD8 T cell response. This combination reversed the immunodominance hierarchy and converted a moderately immunogenic and subdominant CD8 T cell epitope into the immunodominant epitope.

16 Claims, 5 Drawing Sheets

OTHER PUBLICATIONS

Patel et al., A poxvirus-derived vector that directs high levels of expression of cloned genes in mammalian cells, Proc. Natl. Acad. Sci. 85:9431-9435 (1988).

Smith et al., Immunodominance of Poxviral-Specific CTL in a Human Trial of Recombinant-Modified Vaccinia Ankara, Journal of Immunology 175: 8431-8437 (2005).

Sutter et al., Nonreplicating vaccinia vector efficiently expresses recombinant genes, Proc. Natl. Acad. Sci. 89:10847-10851 (1992).

Tscharke et al., Identification of poxvirus CD8+ T cell determinants to enable rational design and characterization of smallpox vaccines, J. Exp. Med. 201:95-104 (2004).

Wyatt et al., Correlation of immunogenicities and in vitro expression levels of recombinant modified vaccinia virus Ankara HIV vaccines, Vaccine 26:486-493 (2008).

Rosel et al., Conserved TAAATG Sequence at the Transcriptional and Translational Initiation Sites of Vaccinia Virus Late Genes Deduced by Structural and Functional Analysis of the HindIII H Genome Fragment, Journal of Virology, 60:436-449 (1986).

Sutter et al., "A recombinant vector derived from the host range-restricted and highly attenuated MVA strain of vaccinia virus stimulates protective immunity inmice to influenza virus," Vaccine 12(11):1032-1040 (1994).

SEQUENCE LISTING

<160> NUMBER OF SEQ ID NOS: 5

<210> SEQ ID NO 1
<211> LENGTH: 247
<212> TYPE: DNA
<213> ORGANISM: Artificial Sequence
<220> FEATURE:
<223> OTHER INFORMATION: Optimized 1xL/5xE Promoter

<400> SEQUENCE: 1
acgcgtgttt aaacgttttg aaaattttt tataataaat atccggtaaa aattgaaaaa    60

```
ctattctaat ttattgcacg gtccggtaaa aattgaaaaa ctattctaat ttattgcacg    120
gtccggtaaa aattgaaaaa ctattctaat ttattgcacg gtccggtaaa aattgaaaaa    180
ctattctaat ttattgcacg gtccggtaaa aattgaaaaa ctattctaat ttattgcacg    240
gtccgga                                                              247

<210> SEQ ID NO 2
<211> LENGTH: 40
<212> TYPE: DNA
<213> ORGANISM: Artificial Sequence
<220> FEATURE:
<223> OTHER INFORMATION: Synthetic pS promoter

<400> SEQUENCE: 2
aaaaattgaa attttatttt ttttttttgg aatataaata                           40

<210> SEQ ID NO 3
<211> LENGTH: 8
<212> TYPE: PRT
<213> ORGANISM: Artificial Sequence
<220> FEATURE:
<223> OTHER INFORMATION: Kb-restricted OVA-derived peptide

<400> SEQUENCE: 3

Ser Ile Ile Asn Phe Glu Lys Leu
1               5

<210> SEQ ID NO 4
<211> LENGTH: 8
<212> TYPE: PRT
<213> ORGANISM: Vaccinia virus

<400> SEQUENCE: 4

Thr Ser Tyr Lys Phe Glu Ser Val
1               5

<210> SEQ ID NO 5
<211> LENGTH: 34
<212> TYPE: DNA
<213> ORGANISM: Vaccinia virus

<400> SEQUENCE: 5
aaaaattgaa aaactagtct aatttattgc acgg                                 34
```

OPTIMIZED EARLY-LATE PROMOTER COMBINED WITH REPEATED VACCINATION FAVORS CYTOTOXIC T CELL RESPONSE AGAINST RECOMBINANT ANTIGEN IN MVA VACCINES

CROSS-REFERENCE TO RELATED APPLICATIONS

This application claims the benefit of U.S. Provisional Application No. 61/159,857, filed Mar. 13, 2009, and EP Appln. No. 09009759.3 filed Jul. 28, 2009, both of which are incorporated herein by reference.

BACKGROUND OF THE INVENTION

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

During the period of 1960 to 1974, Prof. Anton Mayr succeeded in attenuating CVA by over 570 continuous passages in CEF cells (Mayr et al., 1975, Passage History: Abstammung, Eigenschaften and Verwendung des attenuierten Vaccinia-Stammes MVA. Infection 3: 6-14). As part of the early development of MVA as a pre-smallpox vaccine, there were clinical trials using MVA-517 (corresponding to the 517th passage) in combination with Lister Elstree (Stickl, 1974, Smallpox vaccination and its consequences: first experiences with the highly attenuated smallpox vaccine "MVA". Prev. Med. 3(1): 97-101; Stickl and Hochstein-Mintzel, 1971, Intracutaneous smallpox vaccination with a weak pathogenic vaccinia virus ("MVA virus"). Munch Med Wochenschr. 113: 1149-1153) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with conventional vaccinia virus (Mayr et al., 1978, The smallpox vaccination strain MVA: marker, genetic structure, experience gained with the parenteral vaccination and behaviour in organisms with a debilitated defence mechanism (author's transl). Zentralbl. Bacteriol. (B) 167: 375-390). MVA-572 was deposited at the European Collection of Animal Cell Cultures, Vaccine Research and Production Laboratory, Public Health Laboratory Service, Centre for Applied Microbiology and Research, Porton Down, Salisbury, Wiltshire SP4 0JG, United Kingdom, as ECACC V9401 2707.

Being that many passages were used to attenuate MVA, there are a number of different strains or isolates, depending on the passage number in CEF cells. All MVA strains originate from Dr. Mayr and most are derived from MVA-572 that was used in Germany during the smallpox eradication program, or MVA-575 that was extensively used as a veterinary vaccine. MVA-575 was deposited on Dec. 7, 2000, at the European Collection of Animal Cell Cultures (ECACC) with the deposition number V001 20707. The MVA-BN® product used to generate recombinant MVA according to the present invention (MVA-mBN85B) is derived from MVA-584 (corresponding to the 584th passage of MVA in CEF cells).

By serial propagation (more than 570 passages) of the CVA on primary chicken embryo fibroblasts, the attenuated CVA-virus MVA (modified vaccinia virus Ankara) was obtained. MVA was further passaged by Bavarian Nordic and is designated MVA-BN®, corresponding to passage 583. MVA as well as MVA-BN® lacks approximately 13% (26.5 kb from six major and multiple minor deletion sites) of the genome compared with ancestral CVA virus. The deletions affect a number of virulence and host range genes, as well as a large fragment of the gene coding for A-type inclusion protein (ATI) and a gene coding for a structural protein directing mature virus particles into A-type inclusion bodies. A sample of MVA-BN® was deposited on Aug. 30, 2000, at the European Collection of Cell Cultures (ECACC) under number V00083008.

MVA-BN® can attach to and enter human cells where virally-encoded genes are expressed very efficiently. However, assembly and release of progeny virus does not occur. Preparations of MVA-BN® and derivatives have been administered to many types of animals, and to more than 2000 human subjects, including immunodeficient individuals. All vaccinations have proven to be generally safe and well tolerated.

The perception from many different publications is that all MVA strains are the same and represent a highly attenuated, safe, live viral vector. However, preclinical tests have revealed that MVA-BN® demonstrates superior attenuation and efficacy compared to other MVA strains (WO 02/42480). The MVA variant strains MVA-BN® as, e.g., deposited at ECACC under number V00083008, have the capability of reproductive replication in vitro in chicken embryo fibroblasts (CEF), but no capability of reproductive replication in human cells in which MVA 575 or MVA 572 can reproductively replicate. For example, MVA-BN® has no capability of reproductive replication in the human keratinocyte cell line HaCaT, the human embryo kidney cell line 293, the human bone osteosarcoma cell line 143B, and the human cervix adenocarcinoma cell line HeLa. Further, MVA-BN® strains fail to replicate in a mouse model that is incapable of producing mature B and T cells, and as such is severely immune compromised and highly susceptible to a replicating virus. An additional or alternative property of MVA-BN® strains is the ability to induce at least substantially the same level of immunity in vaccinia virus prime/vaccinia virus boost regimes when compared to DNA-prime/vaccinia virus boost regimes.

The term "not capable of reproductive replication" is used in the present application as defined in WO 02/42480 and U.S. Pat. No. 6,761,893, which are hereby incorporated by reference. Thus, the term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

MVA-BN® or its derivatives are, according to one embodiment, characterized by inducing at least substantially the same level of immunity in vaccinia virus prime/vaccinia virus boost regimes when compared to DNA-prime/vaccinia virus boost regimes. A vaccinia virus is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both assays.

WO 02/42480 discloses how vaccinia viruses are obtained having the properties of MVA-BN®. The highly attenuated MVA-BN® virus can be derived, e.g., by the further passage of a modified vaccinia virus Ankara (MVA), such as MVA-572 or MVA-575.

In summary, MVA-BN® has been shown to have the highest attenuation profile compared to other MVA strains and is safe even in severely immunocompromized animals.

Although MVA exhibits strongly attenuated replication in mammalian cells, its genes are efficiently transcribed, with the block in viral replication being at the level of virus assembly and egress. (Sutter and Moss, 1992, Nonreplicating vaccinia vector efficiently expresses recombinant genes. Proc. Natl. Acad. Sci. U.S.A 89: 10847-10851; Carroll and Moss, 1997, Host range and cytopathogenicity of the highly attenuated MVA strain of vaccinia virus: propagation and generation of recombinant viruses in a nonhuman mammalian cell line. Virology 238: 198-211.) Despite its high attenuation and reduced virulence, in preclinical studies MVA-BN® has been shown to elicit both humoral and cellular immune responses to VACV and to the products of heterologous genes cloned into the MVA genome (Harrer et al., 2005, Therapeutic Vaccination of HIV-1-infected patients on HAART with recombinant HIV-1 nef-expressing MVA: safety, immunogenicity and influence on viral load during treatment interruption. Antiviral Therapy 10: 285-300; Cosma et al., 2003, Therapeutic vaccination with MVA-HIV-1 nef elicits Nef-specific T-helper cell responses in chronically HIV-1 infected individuals. Vaccine 22(1): 21-29; Di Nicola et al., 2003, Clinical protocol. Immunization of patients with malignant melanoma with autologous CD34(+) cell-derived dendritic cells transduced ex vivo with a recombinant replication-deficient vaccinia vector encoding the human tyrosinase gene: a phase I trial. Hum Gene Ther. 14(14): 1347-1 360; Di Nicola et al., 2004, Boosting T cell-mediated immunity to tyrosinase by vaccinia virus-transduced, CD34(+)-derived dendritic cell vaccination: a phase I trial in metastatic melanoma. Clin Cancer Res. 10(16): 5381-5390.)

MVA-BN® and recombinant MVA-BN®-based vaccines can be generated, passaged, produced and manufactured in CEF cells cultured in serum-free medium. Many recombinant MVA-BN® variants have been characterized for preclinical and clinical development. No differences in terms of the attenuation (lack of replication in human cell lines) or safety (preclinical toxicity or clinical studies) have been observed between MVA-BN®, the viral vector backbone, and the various recombinant MVA-based vaccines.

Induction of a strong humoral and cellular immune response against a foreign gene product expressed by a VACV vector is hampered by the fact that the foreign gene product has to compete with all of the more than 150 antigens of the VACV vector for recognition and induction of specific antibodies and T cells. The specific problem is the immunodominance of vector CD8 T cell epitopes which prevents induction of a strong CD8 T cell response against the foreign gene product. (Smith et al., Immunodominance of poxviral-specific CTL in a human trial of recombinant-modified vaccinia Ankara. J. Immunol. 175:8431-8437, 2005.) This applies to replicating VACV vectors such as Dryvax, as well as for non-replicating vectors like NYVAC and MVA.

For expression of a recombinant antigen ("neoantigen") by VACV, only poxvirus-specific promoters but not common eukaryotic promoters can be used. The reason for this is the specific biology of poxviruses which replicate in the cytoplasm and bring their own, cell—autonomous transcriptional machinery with them that does not recognize typical eukaryotic promoters.

The viral replication cycle is divided into two major phases, an early phase comprising the first two hours after infection before DNA replication, and a late phase starting at the onset of viral DNA replication at 2-4 hours after infection. The late phase spans the rest of the viral replication cycle from ~2-20 h after infection until progeny virus is released from the infected cell. There are a number of poxviral promoter types which are distinguished and named by the time periods within the viral replication cycle in which they are active, for example, early and late promoters. (See, e.g., Davison and Moss, J. Mol. Biol. 210:771-784, 1989; Davison and Moss, J. Mol. Biol. 210:749-769, 1989; and Hirschmann et al., Journal of Virology 64:6063-6069, 1990, all of which are hereby incorporated by reference.)

Whereas early promoters can also be active late in infection, activity of late promoters is confined to the late phase. A third class of promoters, named intermediate promoters, is active at the transition of early to late phase and is dependent on viral DNA replication. The latter also applies to late promoters, however, transcription from intermediate promoters starts earlier than from typical late promoters and requires a different set of transcription factors.

It became increasingly clear over recent years that the choice of the temporal class of poxviral promoter for neoantigen expression has profound effects on the strength and quality of the neoantigen-specific immune response. It was shown years ago that T cell responses against neoantigens expressed under the control of a late promoter are weaker than those obtained with the same antigen under an early promoter. (Bronte et al., Antigen expression by dendritic cells correlates with the therapeutic effectiveness of a model recombinant poxvirus tumor vaccine. Proc. Natl. Acad. Sci. U.S.A 94:3183-3188, 1997. Couparetal., Temporal regulation of influenza hemagglutinin expression in vaccinia virus recombinants and effects on the immune response. Eur. J. Immunol. 16:1479-1487, 1986.)

Even more strikingly, it was recently shown that in repeated autologous immunizations with VACV as well as with the replication-defective VACV vector MVA, recall CD8 T cell responses against antigens under an exclusively late promoter can fail completely. This failure resulted in an almost undetectable neoantigen-specific CD8 T cell response after the second immunization. (Kastenmuller et al., Cross-competition of CD8+ T cells shapes the immunodominance hierarchy during boost vaccination. J. Exp. Med. 204:2187-2198, 2007.)

Thus, early expression of neoantigens by VACV vectors appears to be crucial for efficient neoantigen-specific CD8 T cell responses. It has also been shown that an early-expressed VACV vector antigen not only competes with late expressed antigens but also with other early antigens for immunodominance in the CD8 T cell response. (Kastenmuller et al., 2007.) The specific properties of the early portion of the poxviral promoter might thus be very important for induction of a neoantigen-specific T cell response. Moreover, it is a commonly held view and a general rule that higher amounts of antigen are beneficial for induction of stronger antigen-specific immune responses (for the poxvirus field, see for example Wyatt et al., Correlation of immunogenicities and in vitro expression levels of recombinant modified vaccinia virus Ankara HIV vaccines. Vaccine 26:486-493, 2008).

A promoter combining 4 early promoter elements and a late promoter element from the ATI gene has been described previously (Funahashi et al., Increased expression in vivo and in vitro of foreign genes directed by A-type inclusion body hybrid promoters in recombinant vaccinia viruses. J. Virol. 65:5584-5588, 1991; Wyatt et al., 2008), and has been shown to direct increased early expression of antigen. However, T cell responses induced by an antigen driven by such a promoter have only been analyzed after a single immunization and were not apparently different from those obtained with the classical p7.5 promoter in this setting. (Funahashi et al., Increased expression in vivo and in vitro of foreign genes directed by A-type inclusion body hybrid promoters in recombinant vaccinia viruses. J. Virol. 65:5584-5588, 1991; Wyatt et al., Correlation of immunogenicities and in vitro expression levels of recombinant modified vaccinia virus Ankara HIV vaccines. Vaccine 26:486-493, 2008.)

Jin et al. Arch. Virol. 138:315-330, 1994, reported the construction of recombinant VACV harbouring promoters consisting of a VACV ATI promoter combined with tandem repeats (2 to 38 copies) of a mutated p7.5 promoter operably linked to the CAT gene. Up to 10 repetitions of the mutated p7.5 promoter were effective in increasing early gene expression. Further repetition appeared to be inhibitory. With all constructs, the amount of CAT protein produced in the presence of cytosine arabinoside (AraC) (i.e. when the viral replication cycle was arrested in the early phase) was less than one-tenth of the amount produced in the absence of AraC (Jin et al. Arch. Virol. 138:315-330, 1994).

Thus, a need in the art exists for compositions and methods capable of achieving high levels of immune responses including CD8 T cell responses against antigens encoded by recombinant MVAs.

BRIEF SUMMARY OF THE INVENTION

The invention encompasses methods for inducing a CD8 T cell response against a neoantigen in a host. In preferred embodiments, the host is administered at least three or four immunizations of a recombinant MVA. Preferably, the recombinant MVA comprises a VACV early/late hybrid promoter linked to a nucleotide sequence encoding an antigen.

In preferred embodiments, after the third boost, an immunodominant T cell response is induced in the host against the encoded antigen. Preferably, the host is a human.

In some embodiments, the recombinant MVA expresses in HeLa cells a level of the encoded antigen from the VACV early/late hybrid promoter in the presence of 40 µg/ml AraC that is greater than the level of the encoded antigen in the absence of AraC. Preferably, the early/late hybrid promoter comprises at least 5 copies of an optimized p7.5 early promoter sequence.

In some embodiments, after the third boost, the recombinant MVA induces a CD8 T cell response in the host against the encoded antigen that is at least 15%, 20%, 25%, or 30% of the total CD8 T cell compartment.

The invention encompasses recombinant MVAs and kits comprising recombinant MVA vectors comprising a VACV early/late hybrid promoter linked to a nucleotide sequence encoding an antigen and instructions to administer the recombinant MVA in at least three administrations to a host.

In preferred embodiments, the early/late hybrid promoter comprises an ATI late promoter linked to at least 5 copies of an optimized p7.5 early promoter sequence. More preferably, the early/late hybrid promoter comprises the nucleotide sequence of SEQ ID NO: 1.

The invention encompasses a recombinant MVA comprising an early/late hybrid promoter linked to a nucleotide sequence encoding an antigen. Preferably, the early/late hybrid promoter comprises an ATI late promoter linked to at least 5 copies of an optimized p7.5 early promoter element. Most preferably, the recombinant MVA expresses in HeLa cells a level of the encoded antigen in the presence of in the presence of 40 µg/ml AraC that is greater than the level of the encoded antigen in the absence of AraC.

DETAILED DESCRIPTION OF THE INVENTION

Figure 1:
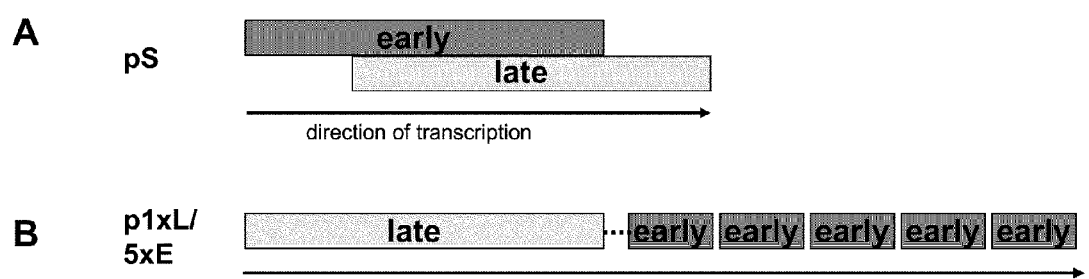
FIGS. 1 A and B are a schematic representation of promoters. The arrangement of early and late promoter elements in pS (A) p1xL/5xE (B) is shown. The bars represent generic early and late elements. Promoter elements are not drawn to scale. The early promoter elements in p1xL/5xE are optimized versions of the early element of the p7.5 promoter.

It was investigated whether a promoter directing expression of the neoantigen as early and as strong as possible would provide the neoantigen with a temporal and quantitative advantage over the majority of autochthonous vector antigens and might thus be beneficial for induction of strong neoantigen-specific CD8 T cell responses.

To design a strong early promoter, a combination of multiple early promoter elements in a tandem fashion were used to enhance expression specifically in the early phase of the viral replication cycle. This promoter element was coupled to a short late promoter element derived from the cowpox ATI promoter which is supposed to direct gene expression in the late phase and would lead to a further increase in the amount of expressed antigen.

The kinetics of expression was directed towards earlier time points using a promoter belonging to the recently defined class of immediate early promoters, the p7.5 promoter. Immediate early genes were defined as being expressed in the period spanning the first hour of the viral infection cycle. (Assarsson et al., Kinetic analysis of a complete poxvirus transcriptome reveals an immediate-early class of genes. Proc. Natl. Acad. Sci. U.S.A 105:2140-2145, 2008; Davison, A. J. and B. Moss. Structure of vaccinia virus early promoters. J. Mol. Biol. 21 0:749-769, 1989.). The p7.5 promoter is composed of a late and an early element and is derived from an immediate early gene.

The early element of the p7.5 promoter was first optimized. Five copies of the optimized p7.5 early promoter element were linked to one copy of an ATI late promoter. Optimization resulted in a promoter with higher expression in the presence of AraC than in the absence of AraC in HeLa cells. Thus, early gene expression was exceedingly high from this promoter.

The ability of a very early expressed neoantigen under control of the optimized promoter to outcompete vector-derived early antigens during secondary responses was investigated by administering the very early expressed neoantigen consecutively in multiple rounds of immunization. Therefore, administration of the MVA containing the optimized promoter was combined with at least two booster immunizations.

Combination of an optimized early/late hybrid promoter directing strongly enhanced early expression of a neoantigen with at least three immunization rounds resulted in a highly efficient neoantigen-specific CD8 T cell response. In the majority of experiments, this approach was even able to reverse immunodominance hierarchy and convert a moderately immunogenic and subdominant CD8 T cell epitope into the immunodominant epitope. This conversion of the immunodominance hierarchy in favour of the neoantigen was not possible to achieve with the well-defined and strong early/late hybrid promoter pS even after four consecutive immunizations.

The invention encompasses recombinant MVA viruses comprising a early/late hybrid promoter linked to a nucleotide sequence encoding an antigen. Preferably, the early/late hybrid promoter comprises at least one late promoter, preferably an ATI promoter, linked to at least two, three, four, five, six, seven, eight, nine, ten, or more copies of an early promoter, preferably an immediate early promoter element, more preferably a p7.5 early promoter element. In preferred embodiments, the encoded antigen is a bacterial, viral, or tumor antigen.

In preferred embodiments, the recombinant MVA expresses high levels of the encoded antigen during the immediate early phase of viral replication. In some embodiments, recombinant MVA expresses in HeLa cells a level of the encoded antigen in the presence of 40 µg/ml AraC that is within 10%, 20%, or 50% of the level of the encoded antigen in the absence of AraC. In preferred embodiments, recombinant MVA expresses in HeLa cells a level of the encoded antigen in the presence of 40 µg/ml AraC that is greater than the level of the encoded antigen in the absence of AraC.

In some embodiments, the early/late hybrid promoter comprises the following sequence:

```
                                          (SEQ ID NO: 1)
5'acgcgtgtttaaacgttttgaaaattttttataataaatatccggta aaaattgaaaaactattctaatttattgcacggtccggtaaaaattgaaa aactattctaatttattgcacggtccggtaaaaattgaaaaactattcta atttattgcacggtccggtaaaaattgaaaaactattctaatttattgca cggtccggtaaaaattgaaaaactattctaatttattgcacggtccgg a 3'.
```

The sequence of the ATI late promoter is in italics, while the 5 copies of the optimized p7.5 early promoter are in bold.

The elements of the 1xL/5xE promoter (SEQ ID NO:1) are as follows:

```
5'acgcgtgtttaaac             MluI/PmeI
(nt 1-14 of SEQ ID NO: 1)    restriction site gttttgaaaatttttttataataaata  ATI late
(nt 15-41 of SEQ ID NO: 1)   promoter tccggt                       Linker
(nt42-47 of SEQ ID NO: 1)

aaaaattgaaaaactattctaatttattgcacgg  P7.5 early
tccggt                              optimized
(nt48-87 of SEQ ID NO: 1)

aaaaattgaaaaactattctaatttattgcacgg  P7.5 early
tccggt                              optimized
(nt 88-127 of SEQ ID NO: 1)

aaaaattgaaaaactattctaatttattgcacgg  P7.5 early
tccggt                              optimized
(nt 128-167 of SEQ ID NO: 1)

aaaaattgaaaaactattctaatttattgcacgg  P7.5 early
tccggt                              optimized
(nt 168-207 of SEQ ID NO: 1)

aaaaattgaaaaactattctaatttattgcacgg  P7.5 early
(nt208-241 of SEQ ID NO: 1)         optimized tccgga 3'                    BspEI
(nt 242-247 of SEQ ID NO: 1). restriction site
```

In some embodiments, the early/late hybrid promoter comprises a sequence that is at least 80%, 85%, 90%, 95%, 98%, or 99% identical to the nucleotide sequence of SEQ ID NO: 1. Based on knowledge of the consensus sequences of early and late promoters, as well as knowledge regarding the effects of various nucleotide substitutions on early and late promoter activity (Davison and Moss, J. Mol. Biol. 210:771-784, 1989; Davison and Moss, J. Mol. Biol. 210:749-769, 1989), many changes to the promoter of SEQ ID NO:1 can be envisioned that would not negatively affect the activity of the promoter. Nucleotide sequences that differ from SEQ ID NO:1 in one or more positions, but have approximately the same (i.e., +/−20%) early and late promoter activity as that of the promoter SEQ ID NO:1 are encompassed by this invention.

The invention encompasses methods of inducing an immunodominant CD8 T cell response in a host. In the context of this invention, an "immunodominant CD8 T cell response" means the major CD8 T cell response of a host against a neoantigen encoded by an MVA vector. Thus, an immunodominant CD8 T cell response against a neoantigen encoded by a recombinant MVA can be generated that is greater than the CD8 T cell response against any MVA viral antigen of the recombinant MVA. The level of the CD8 T cell response can be determined, for example, by the techniques set forth in the examples.

In preferred embodiments, at least three immunizations of a recombinant MVA are administered to the host. In one embodiment, at least four immunizations of a recombinant MVA are administered to the host. Five, six, seven, or more immunizations of a recombinant MVA can be administered to the host. In preferred embodiments, the host is a human.

In preferred embodiments, after the third, fourth, fifth, sixth, seventh, or subsequent boost, an immunodominant T cell response can be induced in the host against the encoded antigen. In some embodiments, after the third, fourth, fifth, sixth, seventh, or subsequent boost, the recombinant MVA induces a CD8 T cell response in the host against the encoded antigen that comprises at least 15%, 20%, 25%, 30%, or 35% of total CD8 T cells.

In preferred embodiments, the recombinant MVA comprises a VACV early/late hybrid promoter linked to a nucleotide sequence encoding an antigen. Preferably, the early/late hybrid promoter comprises at least one ATI, or another late promoter linked to at least two, three, four, five, six, seven, eight, nine, ten, or more copies of an optimized p7.5 early promoter element.

In preferred embodiments, the encoded antigen is a bacterial, viral, or tumor antigen. Preferably, the antigen is a foreign antigen to the host.

Recombinant MVAs Comprising a Hybrid Early/Late Promoter

The invention encompasses a recombinant MVA vector comprising a VACV early/late hybrid promoter linked to a nucleotide sequence encoding an antigen. Preferred early/late hybrid promoters comprise multiple copies of an optimized p7.5 early promoter.

Modified Vaccinia Ankara Viruses

The invention encompasses recombinant MVA viruses generated with any and all MVA viruses. Preferred MVA viruses are MVA variant strains MVA-BN® as, e.g., deposited at ECACC under number V00083008; MVA-575, deposited on Dec. 7, 2000, at the European Collection of Animal Cell Cultures (ECACC) with the deposition number V001 20707; and MVA-572, deposited at the European Collection of Animal Cell Cultures as ECACC V9401 2707. Derivatives of the deposited strain are also preferred.

Preferably, the MVA has the capability of reproductive replication in vitro in chicken embryo fibroblasts (CEF), but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa.

In preferred embodiments, the Modified vaccinia virus Ankara (MVA) virus is characterized by having the capability of reproductive replication in vitro in chicken embryo fibroblasts (CEF) and by being more attenuated than MVA-575 in the human keratinocyte cell line HaCaT, in the human bone osteosarcoma cell line 143B, and in the human cervix adenocarcinoma cell line HeLa. Preferably, the MVA virus is capable of a replication amplification ratio of greater than 500 in CEF cells.

Promoters

In preferred embodiments, the recombinant MVA comprises an early/late hybrid promoter. An early/late hybrid promoter drives expression of a linked nucleic acid sequence at both early and late times of the viral lifecycle.

The late promoter can be any late promoter that functions to drive late expression within the recombinant MVA. Preferably, an ATI promoter is used.

The early promoter can be any early promoter that functions to drive early expression within the recombinant MVA. Preferably, an immediate early promoter is used. More preferably, a p7.5 early promoter element is used.

The early promoter is preferably optimized to maximize early gene expression. An optimized p7.5 promoter has the sequence of SEQ ID NO:1 compared to the wild-type sequence of SEQ ID NO:5:

```
aaaaattgaaaaactattctaatttattgcacgg  (nt48-87 of SEQ
                                     ID NO: 1)

aaaaattgaaaaactagtctaatttattgcacgg  (SEQ ID NO: 5)
```

Most preferably, the promoter is optimized by having an "A" residue at nt 5, a "T" residue at nt 7, an "A" residue at nt 13, and a "C" residue at nt 14 of SEQ ID NO:5 in the p7.5 early promoter.

Most preferably, the early promoter comprises at least two, three, four, five, six, seven, eight, nine, ten, or more copies of a p7.5 early promoter element. Preferably, the early promoter is linked to an ATI late promoter to generate a hybrid early/late promoter.

In a preferred embodiment, the recombinant MVA comprises the early/late hybrid promoter of SEQ ID NO:1. In other embodiments, the recombinant MVA comprises an early/late hybrid promoter that comprises a sequence that is at least 80%, 85%, 90%, 95%, 98%, or 99% identical to SEQ ID NO: 1.

The percent identity may be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

Preferably, a early/late hybrid promoter comprises a sequence that is at least 80%, 85%, 90%, 95%, 98%, or 99% identical to SEQ ID NO: 1, or to nt 15-41 or nt 48-81, nt 48-87, or nt 48-247 of SEQ ID NO:1, and has approximately the same (i.e., +/−20%) early and late promoter activity as the promoter of SEQ ID NO:1.

Antigens

Any antigen, including those that induce a T-cell response, can be expressed by the recombinant MVA of the invention. Viral, bacterial, fungal, and cancer antigens are preferred. HIV-1 antigens, Dengue virus antigens, prostate-specific antigen (PSA) and prostatic acid phosphatase (PAP) antigen, HER2/Neu antigens, anthrax antigens, measles virus antigens, influenza virus, picorna virus, corona virus and respiratory syncytial virus antigens are particularly preferred antigens. Preferably, the antigen is a foreign antigen.

Antigen Expression Levels

Due to the presence of a hybrid early/late promoter, the recombinant MVAs of the invention express recombinant antigens during the early and late phases of the viral replication cycle.

Early and late expression from the hybrid early/late promoter can be determined by infecting CEF and Hela cells, for example, as illustrated in the examples. The levels can be compared to the expression levels with the p1xL/5xE promoter (SEQ ID NO:1) or the pS promoter (SEQ ID NO:2) in the presence and absence of AraC, for example, at 40 μg/ml. Recombinant MVA vectors with early expression levels similar to, or increased over, vectors with the p1xL/5xE promoter can provide similar in vivo results with respect to immunodominance of the expressed antigen.

In various embodiments, the recombinant MVA expresses in HeLa cells a level of the encoded antigen in the presence of 40 μg/ml cytosine arabinoside (AraC) that is at least 50%, 66%, 75%, 80%, 85%, 90%, 95%, or 100% of the level of the encoded antigen in the absence of AraC.

In various embodiments, the recombinant MVA expresses in HeLa cells a level of the encoded antigen in the presence of 40 μg/ml AraC that is greater than the level of the encoded antigen in the absence of 40 μg/ml AraC.

In various embodiments, the recombinant MVA expresses two-fold, three-fold, or four-fold higher levels of the encoded antigen than an MVA vector with the pS promoter driving expression in HeLa and/or CEF in the presence of 40 μg/ml AraC.

Kits Comprising Recombinant MVA

The invention provides kits comprising the recombinant MVA virus according to the present invention. The kit can comprise at least one, two, three, four, or more containers or vials of the recombinant MVA virus, together with instructions for the administration of the virus to a subject. In a preferred embodiment, the subject is a human. The instructions can indicate that the recombinant MVA virus is administered to the subject in multiple (i.e., 2, 3, 4, 5, 6, etc.) dosages at specific timepoints (e.g., at least 4 weeks, at least 6 weeks, at least 8 weeks after the previous administration). Preferably, the instructions indicate that the recombinant MVA is to be administered in at least 3 or at least 4 dosages.

Methods of Inducing a CD8 T Cell Response

The invention encompasses methods of inducing a CD8 T cell response in a host. In preferred embodiments, the method comprises administering at least three, four, or five immunizations of a recombinant MVA comprising a hybrid early/late hybrid promoter to the host.

Administration to a Host

The recombinant MVA virus according to the invention can be used for the treatment of a wide range of mammals including humans and even immune-compromised humans. Hence, the present invention also provides a pharmaceutical composition and also a vaccine for inducing an immune response in a living animal body, including a human.

The vaccine preferably comprises the recombinant MVA viruses in a concentration range of $10^4$ to $10^9$ TCID (tissue culture infectious dose) $_{50}$/ml, preferably in a concentration range of $10^5$ to $5 \times 10^8$ TCID$_{50}$/ml, more preferably in a concentration range of $10^6$ to $10^8$ TCID$_{50}$/ml, and most preferably in a concentration range of $10^7$ to $10^8$ TCID$_{50}$/ml, especially $10^8$ TCID$_{50}$/ml.

A preferred vaccination dose for humans comprises $10^6$ to $10^9$ TCID$_{50}$, most preferably a dose of $10^7$ TCID$_{50}$ or $10^8$ TCID$_{50}$, especially $10^8$ TCID$_{50}$.

The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the recombinant MVA virus according to the invention can be converted into a physiologically acceptable form. This can be done based on the experience in the preparation of poxvirus vaccines used for vaccination against smallpox (as described by Stickl et al. 1974).

For example, the purified virus can be stored at −80° C. with a titre of $5 \times 10^8$ TCID$_{50}$/ml formulated in about 10 mM Tris, 140 mM NaCl pH 7.4. For the preparation of vaccine shots, e.g., $10^2$-$10^8$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, or any other path of administration know to the skilled practitioner. The mode of administration, the dose and the number of administrations can be optimized by those skilled in the art in a known manner. However, most commonly a patient is vaccinated with a second administration about one month to six weeks after the first vaccination administration. Third, fourth, and subsequent administrations will most commonly be about one month to six weeks after the previous administration.

The invention provides methods for immunizing an animal body, including a human. In one embodiment a subject mammal, which includes rats, rabbits, mice, and humans are immunized comprising administering a dosage of a recombinant MVA to the subject, preferably to a human. In one embodiment, the first dosage comprises $10^8$ TCID$_{50}$ of the recombinant MVA virus and the second and additional dosages (i.e., third, fourth, fifth, etc.) comprise $10^8$ TCID$_{50}$ of the virus.

The immunization can be administered either systemically or locally, i.e. parenteral, subcutaneous, intravenous, intramuscular, or any other path of administration known to the skilled practitioner.

CD8 T Cell Responses

Immunizations with the recombinant MVA of the invention can induce robust CD8 T cell responses. In preferred embodiments, after the third, fourth, fifth, etc. boost, the recombinant MVA induces a CD8 T cell response in the host against the encoded antigen that is greater than the CD8 T cell response against the CD8 T cell epitope TSYKFESV (SEQ ID NO:4) encoded by the MVA vector. Preferably, after the third, fourth, fifth, etc. boost, an immunodominant T cell response is induced in the host against the encoded antigen. Preferably, a moderately immunogenic and subdominant CD8 T cell epitope is converted into the immunodominant epitope. Most preferably, after the third, fourth, fifth, etc. boost, the recombinant MVA induces a CD8 T cell response in the host against the encoded antigen that is at least 10%, 15%, 20%, 25%, 30%, or 35% of total CD8 T cells. Preferably, after the third, fourth, fifth, etc. boost, the recombinant MVA increases the CD8 T cell response in the host against the encoded antigen at least 2-, 3-, 4-, 5-, or 10-fold (i.e., from 1% to 2%, 3%, 4%, 5%, or 10% of total CD8 T cells) as compared to the response with the encoded antigen after a single administration or increases the CD8 T cell response in the host against the encoded antigen at least 2-, 3-, 4-, 5-, or 10-fold as compared to the T cell response of a viral late antigen (e.g. B8R). Most preferably, the CD8 T cell response in the host against the encoded antigen increases with 2-, 3-, 4-, or 5-, etc. immunizations to a greater extent than the response against a viral late antigen (e.g. B8R).

The level of CD8 T cell response can be determined by collecting blood from an immunized host and separating peripheral blood mononuclear cells (PBMC). These can be resuspended in growth medium containing 5 μg/ml brefeldin A (BFA, "GolgiPlug", BD Biosciences) with 1 μM of test peptides, including peptides against immunodominant MVA epitopes (i.e., TSYKFESV; SEQ ID NO:4) ("B8R") and peptides derived from the expressed neoantigen. The PBMC can then be incubated for 5 h at 37° C. in 5% CO2, harvested, resuspended in 3 ml cold PBS/1 0% FCS/2 mM EDTA and stored overnight at 4° C. The following day, the PBMC can be stained with antibodies anti-CD8a-Pac-Blue (clone 53-6.7), anti-CD62L-PE-Cy7, anti-CD44-APCAlexa 750, and anti-CD4-PerCP-Cy5.5 (all antibodies from BD Biosciences). The PBMC can be incubated with appropriate dilutions of the indicated antibodies for 30 min at 4° C. in the dark. After washing, cells can be fixed and permeabilized by using the Cytofix/Cytoperm™ Plus kit (BD Biosciences) according to the manufacturer's instructions. After washing, PBMC can stained for intracellular interferon-γ (IFN-γ) using a FITC-conjugated anti-I FN-y antibody (BD biosciences) diluted in perm/wash buffer (BD Biosciences). Stained cells can be analysed by flow cytometry.

EXAMPLES

Example 1

Generation of MVA Recombinants

A synthetic late/early promoter designated p1xL/5xE containing a late element and five tandemly arranged early promoter elements was constructed (FIG. 1) and is designated "early/late hybrid promoter" throughout. The late element was derived from the promoter directing the expression of the A-type inclusion (ATI) protein. The five early elements are all identical and were derived from the immediate early p7.5 promoter. They were further optimized according to the consensus sequence for early vaccinia virus promoters. (Broyles, S. S., Vaccinia virus transcription. J. Gen. Virol. 84:2293-2303, 2003; Chakrabarti, S., J. R. Sisler, and B. Moss, Compact, synthetic, vaccinia virus early/late promoter for protein expression. Biotechniques 23:1094-1097, 1997; Davison and Moss, J. Mol. Biol. 210:749-769, 1989.)

This promoter was compared with the well-defined synthetic "pS" promoter (FIG. 1) constructed by Chakrabarti et al., 1997, which has been shown to direct high level gene expression. These promoter constructs were fused to the open reading frames of either chicken ovalbumine (OVA) or enhanced green fluorescent protein (eGFP) and the resulting constructs were used to generate the respective recombinant MVA viruses by homologous recombination into intergenic region MVA07/08 to obtain MVA-p1xL/5xE-OVA expressing OVA under control of the p1xL/5xE promoter and MVA-pS-OVA expressing OVA under control of the synthetic pS promoter (aaaaattgaa attttatttt ttttttttgg aatataaata; SEQ ID NO:2).

Example 2

Promoter-Dependent Gene Expression Levels In Vitro

The expression efficiency of the eGFP reporter gene under control of promoters pS and p1xL/5xE was determined using cell cultures infected with the respective recombinant MVA viruses.

Figure 2:
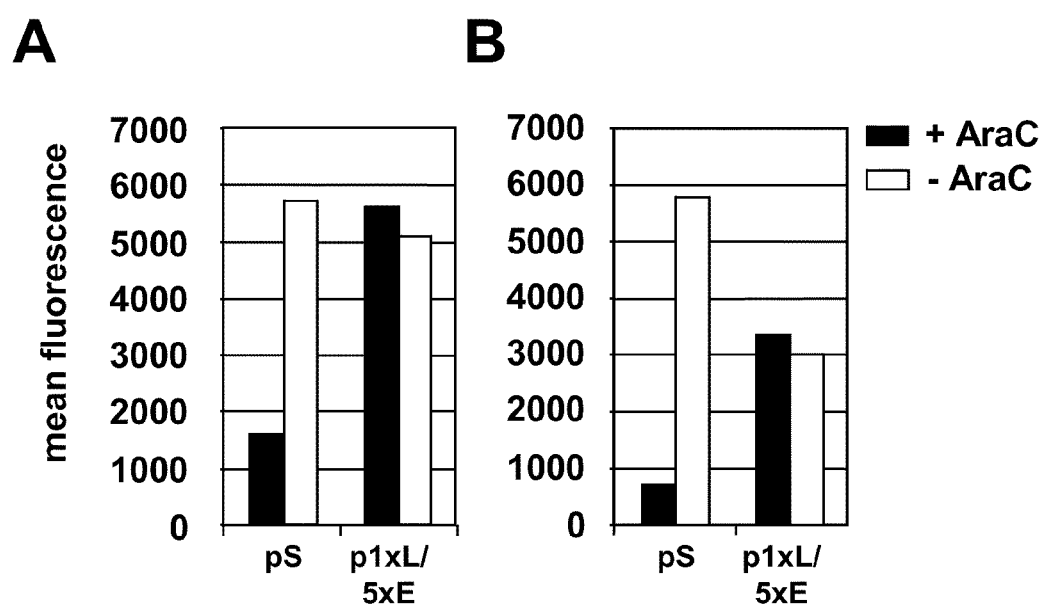
FIGS. 2 A and B depict expression of eGFP directed by recombinant MVAs. Recombinant MVAs containing the eGFP open reading frame under control of the indicated promoters were used to infect HeLa (A) and CEF cells (B) at a multiplicity of infection (m.o.i.) of 5. Cells were either treated with cytosine arabinoside (AraC) in a concentration of 40 µg/ml (+AraC) or were left untreated (−AraC) during infection. Cells were harvested 16 h post infection (p.i.) by trypsinization and analyzed by flow cytometry for eGFP expression. Dead cells were excluded by propidium iodide staining.

The pS promoter appeared to direct higher expression than the p1xL/5xE promoter in untreated cells permissive for MVA (CEF, FIG. 2B). In contrast, eGFP expression in untreated non-permissive cells was similar with both promoters (FIG. 2A). Non-permissive cells supposedly mimic the in vivo situation of MVA infection more accurately than the permissive CEF cells suggesting that overall expression directed by the two promoters in vivo might be similar. Importantly, the p1xL/5xE promoter directed much higher early eGFP expression than the pS promoter when infection was arrested in the early phase by AraC treatment (FIG. 2), indicating that the early portion of p1xL/5xE was stronger than that of the pS promoter, suggesting that proteins expressed under control of the p1xL/5xE promoter might induce stronger T cell responses. With both promoters, eGFP expression was already detectable at 2 h p.i.

Example 3

Analysis of CD8 T Cell Responses

CD8 T cell responses against recombinantly expressed OVA under control of the promoters pS and p1xL/5xE were determined in C57BL/6 mice after one, two, and three immunizations with $10^8$ TCID$_{50}$ recombinant MVA per mouse. The OVA-specific CD8 T cell response was determined by assessing the number of CD8 T cells secreting IFN-γ following a 5-hour stimulation with the K$^b$-restricted OVA-derived peptide SIINFEKL (OVA$_{257-268}$ SIINFEKL; SEQ ID NO:3). To monitor the CD8 T cell response to the MVA vector, CD8 T cells secreting IFN-γ upon recognition of the immunodominant CD8 T cell epitope of MVA (Tscharke et al., JEM 201: 95-104, 2005) derived from the viral B8R protein (B8R20-27TSYKFESV; SEQ ID NO:4) were quantitated.

Briefly, immunized animals were bled from the tail vein and 120 μl of blood per mouse was resuspended in 2 ml of PBS pH 7.4 containing 4% fetal calf serum (FCS), 2 mM ethylenediaminetetraacetic acid (EDTA) and 2.5 U/ml heparin. Blood samples were split into three aliquots and red blood cells were lysed using Red Blood Cell Lysing Buffer (Sigma). Peripheral blood mononuclear cells (PBMC) were finally resuspended in 2 ml of RPMI supplemented with 10% FCS and 0.05 mM R-mercaptoethanol containing 5 μg/ml brefeldin A (BFA, "GolgiPlug", BD Biosciences) and 1 μM of peptides SIINFEKL (SEQ ID NO:3) ("OVA"), TSYKFESV (SEQ ID NO:4) ("B8R"), or no peptide. Peptides were purchased from ProImmune (Oxford, UK). PBMC were then incubated for 5 h at 37° C. in 5% CO2, harvested, resuspended in 3 ml cold PBS/1 0% FCS/2 mM EDTA and stored overnight at 4° C. The following day, PBMC were stained with antibodies anti-CD8a-Pac-Blue (clone 53-6.7), anti-CD62L-PECy7, anti-CD44-APC-Alexa 750, and anti-CD4-PerCP-Cy5.5 (all antibodies from BD Biosciences). PBMC were incubated with appropriate dilutions of the indicated antibodies for 30 min at 4° C. in the dark. After washing, cells were fixed and permeabilized by using the Cytofix/Cytoperm™ Plus kit (BD Biosciences) according to the manufacturer's instructions. After washing, PBMC were stained for intracellular interferon-γ (IFN-γ) using a FITC-conjugated anti-IFN-γ antibody (BD biosciences) diluted in perm/wash buffer (BD Biosciences). Stained cells were analysed by flow cytometry on a BD Biosciences LSR II system.

Figure 3:
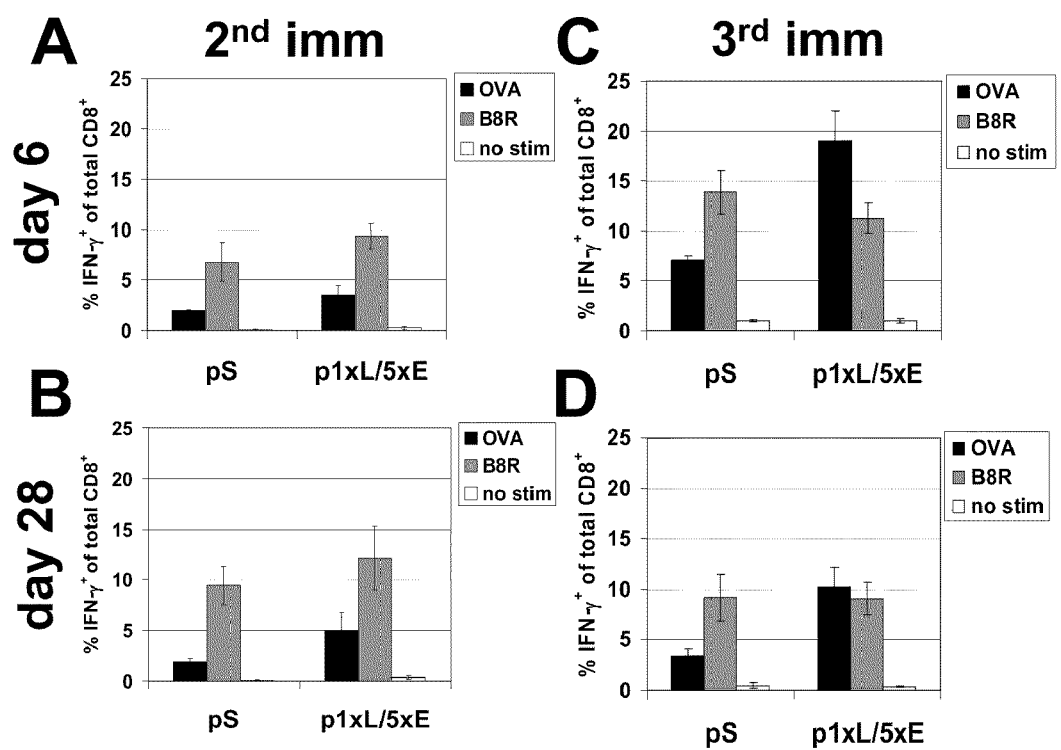
FIG. 3 A-D depict induction of OVA-specific CD8 T cell responses by recombinant VACV. MVA-p1xL/5xE-OVA and MVA-pS-OVA were used to infect BALB/c mice intraperitoneally (i.p.) at a dose of $10^8$ $TCID_{50}$ per mouse. Mice were boosted with a second and third i.p. injection at 28 and 56 days, respectively, after the first immunization. Blood was analyzed at 6 (A, C) and 28 (B, D) after $2^{nd}$ (A, B) and $3^{rd}$ immunization (C, D) for induction of OVA-specific and vector-specific CD8 T cell responses. Vector-specific responses were assessed by using an immunodominant peptide epitope derived from the viral B8R protein. Analysis of antigen-specific cells was performed by intracellular cytokine staining for IFN-γ. Indicated are the percentages of OVA- and B8R-specific cells among total CD8 T cells.

Similar proportions of OVA-specific and B8R-specific CD8 T cells were observed independent of the type of promoter after the first and second immunization when determined on two different time points after immunization with recombinant MVA (FIG. 3A, B). A slightly higher number of OVA-specific CD8 T cells was observed after immunization with the OVA construct containing the p1xL/5xE promoter compared to the pS-OVA construct. The ratio of B8R-specific to OVA-specific CD8 T cells was between 2 to 3 for both constructs (FIG. 3A, B) confirming that B8R remained the immunodominant epitope after the first (data not shown) and second immunization (FIG. 3A, B) under conditions of recombinant co-expression of an antigen (OVA) containing a moderately immunogenic CD8 T cell epitope.

Strikingly, more than two times stronger OVA-specific CD8 T cell responses were observed on day 6 after the third immunization with MVA-p1xL/5xE-OVA compared to triple immunization with MVA-pS-OVA (FIG. 3C). The proportion of OVA-specific CD8 T cells reached a remarkable 19% of all CD8 T cells with MVA-p1xL/5xE-OVA (FIG. 3C). Surprisingly, significantly more OVA-specific CD8 T cells than B8R-specific CD8 T cells were detectable in the majority of experiments after the third immunization with MVA-p1xL/5xE compared to triple immunization with MVA-pS-OVA (FIG. 3C). After the third immunization with the latter, B8R-specific CD8 T cells were still predominant (FIG. 3C). The neoantigen OVA containing a moderate CD8 T cell epitope represented the immunodominant CD8 T cell antigen after the third boost with MVA-p1xL/5xE-OVA in the majority of experiments instead of the formerly immunodominant B8R-derived epitope from the MVA vector. Thus, a reversal of the immunodominance hierarchy could be achieved by using the p1xL/5xE promoter for expression of the neoantigen, but not by using the pS promoter.

In the early memory phase at 28 days after the third immunization with MVA-p1xL/5xE, OVA$_{257-268}$ still represented the immunodominant epitope in most experiments and about two-fold more OVA-specific CD8 T cells were present compared to mice immunized three times with MVA-pS-OVA (FIG. 3D). The superior effect of MVA-p1xL/5xE-OVA over MVA-pS-OVA on induction of OVA-specific CD8 T cells was statistically significant using a two-way repeated measures ANOVA test (p=0.012) taking into consideration the effect all four time points (FIG. 3A-D) of analysis after second and third immunization. (p=0.012). In contrast, B8R-specific CD8 T cell responses were not significantly different over the 2nd and 3rd immunization between the two MVA vectors (p=0.71).

Figure 4:
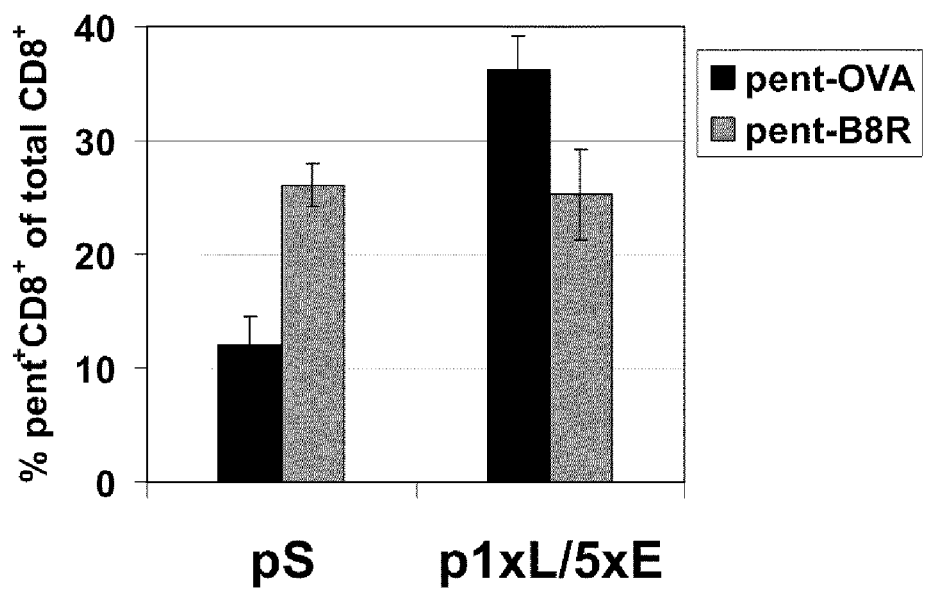
FIG. 4 depicts OVA-specific CD8 T cell memory 85 days after 3rd immunization. Blood of mice described in FIG. 3 was analyzed 85 days after the third immunization with MVA-pS-OVA and MVA-p1xL/5xE-OVA for presence of OVA and B8R-specific CD8 T cells by staining with fluorescence-labelled MHC I pentamers $K^b$/OVA and $K^b$/B8R. Indicated is the percentage of pentamer-positive cells among total CD8 T cells.

Analysis of the long-term memory in blood of mice 85 days after the third immunization using OVA$_{257-268}$ SIINFEKL (SEQ ID NO:3)- and B8R$_{20-27}$ TSYKFESV (SEQ ID NO:4)-specific MHC class I pentamers demonstrated that OVA-specific CD8 T cells were still immunodominant on most experiments when immunizations had been performed with MVA-p1xL/5xE-OVA (FIG. 4). In contrast, B8R was always still the immunodominant antigen when MVA-pS-OVA had been used (FIG. 4). Approximately 80% of all OVA specific CD8 T cells were of the effector memory phenotype irrespective of the promoter use.

Example 4

Effect of Four Immunizations

Figure 5:
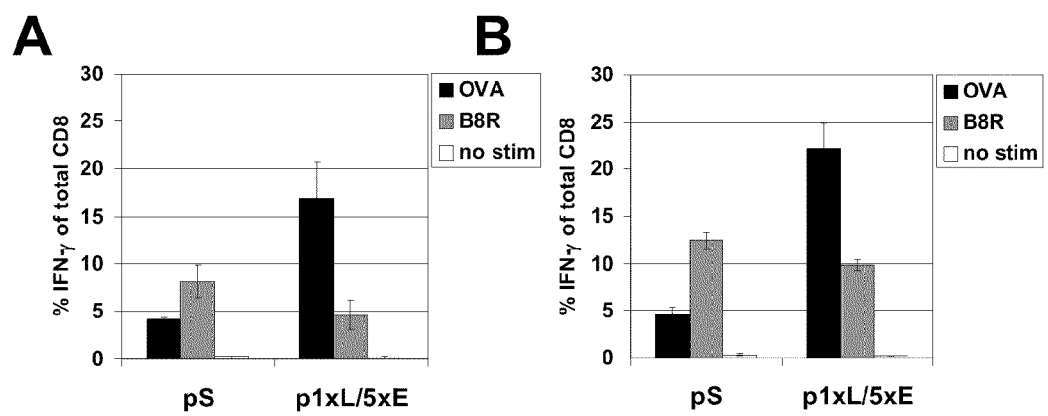
FIG. 5 depicts CD8 T cell responses in blood and spleen after four immunizations. Three of the five mice immunized three times with MVA-p1xL/5xE-OVA and five mice immunized three times with MVA-pS-OVA were immunized a fourth time with $10^8$ $TCID_{50}$ of MVA-p1xL/5xE-OVA and MVA-pS-OVA, respectively, 99 days after the last immunization. Blood (A) and splenocytes (B) were analyzed at six days after the fourth immunization for induction of OVA-specific and B8R-specific CD8 T cell responses by intracellular cytokine staining for IFN-γ. Indicated are the percentages of OVA- and B8R-specific cells among total CD8 T cells.

Three of the five mice immunized three times with MVA-p1xL/5xE-OVA and five mice immunized three times with MVA-pS-OVA were immunized a fourth time with the respective OVA-expressing MVA recombinants 99 days after the last immunization. The percentage of IFN-γ secreting OVA-specific CD8 T cells in the blood did not increase further when determined six days after the fourth immunization using either of the MVA recombinants (FIG. 5A). Importantly, OVA did not become the immunodominant epitope even after four immunizations with MVA-pS-OVA, whereas the reversed immunodominance pattern with a much stronger OVA-specific than B8R-specific CD8 T cell response remained stable with MVA-p1xL/5xE-OVA after an additional (fourth) immunization (FIG. 5A). The immunodominance pattern in peripheral blood truly reflected the situation in spleen representing a secondary lymphoid organ, since splenocytes from MVA-p1xL/5xE-OVA-immunized mice after four vaccinations showed a very similar ratio of OVA-specific to B8R-specific CD8 T cells like the CD8 T cells from blood (FIG. 5A, B). In the spleen, there was an even higher proportion of OVA-specific CD8 T cells than in blood reaching over 22% of all splenic CD8 T cells.

We claim:

1. A method of inducing a CD8 T cell response in a host comprising administering at least three immunizations of a recombinant modified vaccinia Ankara virus (MVA) to the host;
   wherein the recombinant MVA comprises a Vaccinia virus (VACV) early/late hybrid promoter linked to a nucleotide sequence encoding an antigen;
   wherein, after the third immunization, the recombinant MVA induces a CD8 T cell response in the host against the encoded antigen that is at least 15% of total CD8 T cells.

2. The method of claim 1, wherein the host is a human.

3. The method of claim 1, wherein the recombinant MVA expresses in HeLa cells a level of the encoded antigen from the VACV early/late hybrid promoter in the presence of 40 μg/ml AraC that is greater than the level of the encoded antigen in the absence of AraC.

4. The method of claim 3, wherein the host is a human.

5. The method of claim 1, wherein the early/late hybrid promoter comprises at least 5 copies of an optimized p7.5 early promoter element.

6. The method of claim 5, wherein the host is a human.

7. The method of claim 1, wherein, after the third immunization, the recombinant MVA induces a CD8 T cell response in the host against the encoded antigen that is at least 25% of total CD8 T cells.

8. The method of claim 7, wherein the host is a human.

9. The method of claim 1, wherein, after the third immunization, the recombinant MVA induces a CD8 T cell response in the host against the encoded antigen that is at least 30% of total CD8 T cells.

10. The method of claim 1 comprising administering at least four immunizations of a recombinant MVA to the host.

11. The method of claim 10, wherein the host is a human.

12. The method of claim 11, wherein the host is a human.

13. A kit comprising a recombinant MVA vector comprising a VACV early/late hybrid promoter linked to a nucleotide sequence encoding an antigen and instructions to administer the recombinant MVA in at least three administrations to a host, wherein the recombinant MVA expresses in HeLa cells a level of the encoded antigen in the presence of 40 µg/ml AraC that is greater than the level of the encoded antigen in the absence of AraC.

14. The kit of claim 13, wherein the early/late hybrid promoter comprises an ATI late promoter linked to at least 5 copies of an optimized p7.5 early promoter element.

15. The kit of claim 13, wherein the early/late hybrid promoter comprises the nucleotide sequence of SEQ ID NO: 1.

16. A recombinant MVA comprising an early/late hybrid promoter linked to a nucleotide sequence encoding an antigen,
 wherein the early/late hybrid promoter comprises an ATI late promoter linked to at least 5 copies of an p7.5 early promoter element,
 wherein the recombinant MVA expresses in HeLa cells a level of the encoded antigen in the presence of in the presence of 40 µg/ml AraC that is greater than the level of the encoded antigen in the absence of AraC.

* * * * *

UNITED STATES PATENT AND TRADEMARK OFFICE
CERTIFICATE OF CORRECTION

| | | |
|---|---|---|
| PATENT NO. | : 8,394,385 B2 | Page 1 of 1 |
| APPLICATION NO. | : 12/719987 | |
| DATED | : March 12, 2013 | |
| INVENTOR(S) | : Hausmann et al. | |

It is certified that error appears in the above-identified patent and that said Letters Patent is hereby corrected as shown below:

In the Claims:

Col. 20:

Lines 8-9, please delete the second occurrence of "in the presence of".

Signed and Sealed this
Twentieth Day of August, 2013

Teresa Stanek Rea
*Acting Director of the United States Patent and Trademark Office*